United States Patent
Osborne et al.

(10) Patent No.: US 7,704,959 B2
(45) Date of Patent: Apr. 27, 2010

(54) AZITHROMYCIN FOR THE TREATMENT OF NODULAR ACNE

(75) Inventors: David Wade Osborne, Santa Rosa, CA (US); Gordon Jay Dow, Santa Rosa, CA (US); Bhaskar Chaudhuri, San Jose, CA (US); Barry Calvarese, Menlo Park, CA (US)

(73) Assignee: Dow Pharmaceutical Sciences, Petaluma, CA (US)

( * ) Notice: Subject to any disclaimer, the term of this patent is extended or adjusted under 35 U.S.C. 154(b) by 400 days.

(21) Appl. No.: 11/635,127

(22) Filed: Dec. 6, 2006

(65) Prior Publication Data

US 2008/0081790 A1 Apr. 3, 2008

Related U.S. Application Data

(60) Provisional application No. 60/849,065, filed on Oct. 3, 2006.

(51) Int. Cl.
*A61K 31/70* (2006.01)
(52) U.S. Cl. ....................................................... 514/29
(58) Field of Classification Search .................... 514/29
See application file for complete search history.

(56) References Cited

U.S. PATENT DOCUMENTS 6,015,568 A 1/2000 Segot
6,958,153 B1 10/2005 Ormerod

OTHER PUBLICATIONS

Dionisio, et al, Chronic cryptosporidiosis in patients with AIDS: stable remission and possible eradication after long term, low dose . . . , J. Clin. Pathol., 51:138-142 (1998).
Elewski, A novel treatment for acne vulgaris and rosacea, European Academy of Dermatology and Venerology, JEADV, 14:423-424 (2000).
Fernandez-Obregon, Azithromycin for the treatment of acne, International Journal of Dermatology, 39:45-50 (2000).
Gruber, Azithromycin compared with minocycline in the treatment of acne comedonica and papulo-pustulosa, Journal of Chemotherapy, 10(6):469-473 (1998).
Kapadia, Acne treated successfully with azithromycin, International Journal of Dermatology, 43:766-767 (2004).
Kunynetz, Systemic antibiotic therapy for acne: A review, Skin Therapy Letter, 7(5):3-8 (2002).
Kus, Comparison of efficacy of azithromycin vs. doxycycline in the treatment of acne vulgaris, Clinical and Experimental Dermatology, 30:215-220 (2005).
McHugh, A topical azithromycin preparation for the treatment of acne vulgaris and rosacea, Journal of Dermatological Treatment, 15:295-302 (2004).
Singhi, Comparison of oral azithromycin pulse with daily doxycycline in the treatment of acne vulgaris, Indian Journal of Dermatology, Venerology . . . , 60(4):274-276 (2003).
Webster, Ance vulgaris, British Medical Journal (BMJ), 325:475-479 (2002).
Zouboulis, C.C. And Piquero-Martin, J., "Update and Future of Systemic Acne Treatment," Dermatology, 206:37-53 (2003.
Rafiei, R., and Yaghoobi, R., "Azithromycin verus tetracycline in the treatment of acne vulgaris," Journal of Dermatologic Treatment, 17:217-221 (2006).
Innocenzi, D., et al, "Acne giovanile di grado moderato: efficacia, tollerabilita, e compliance di un trattamento di 12 settimane . . . ," Derm. Clin. 25(3):126-130 (2005).

*Primary Examiner*—Elli Peselev
(74) *Attorney, Agent, or Firm*—Howard Eisenberg, Esq.

(57) ABSTRACT

Azithromycin, administered systemically, is an effective treatment for nodules associated with acne vulgaris.

16 Claims, No Drawings

AZITHROMYCIN FOR THE TREATMENT OF NODULAR ACNE

This application claims the benefit of U.S. Provisional Patent Application Ser. No. 60/849,065, which was filed on Oct. 3, 2006, the disclosure of which is incorporated herein in its entirety by reference.

FIELD OF THE INVENTION

The invention pertains to the field of antibiotic therapy, particularly azithromycin, to combat skin disease and particularly to the use of azithromycin to treat acne vulgaris. In particular, the invention pertains to the field of the treatment of acne nodules, such as due to nodular acne, and most particularly to the treatment of severe nodular acne vulgaris.

BACKGROUND OF THE INVENTION

Acne vulgaris, often referred to simply as acne, is a common skin disease that typically, although not exclusively, affects adolescents. When untreated, most cases of acne persist for several years and then spontaneously remit, usually when an individual is in the mid-twenties.

The etiology of acne is multi-factorial. The disease is thought to originate primarily due to increased production of sebum, hypercornification of the infundibulum of pilosebaceous glands, proliferation of microbial flora especially *Propionibacterium acnes*, and subsequent inflammation. The normal process of epidermal maturation, called keratinization, involves the growing and shedding of cells that line the pores and glands of the skin. In acne, this process is disrupted, causing an overproduction of epithelial cells (hyperkeratosis) in the follicular infundibulum of the sebaceous gland duct, forming a blockage of the pore.

The resulting lesions can be divided into inflammatory and non-inflammatory lesions. Non-inflammatory lesions, classified as open and closed comedones, are commonly known as blackheads and whiteheads, respectively. Cases of acne presenting solely non-inflammatory lesions are sometimes referred to as mild acne.

Inflammatory lesions are a result of excessive growth of the common bacteria, *Propionibacterium acnes*, and its interaction with the normal oils of the skin (sebum), resulting in the generation of byproducts that elicit an inflammatory reaction. In addition to these primary lesions, patients may also suffer from scars as a complication of inflammatory lesions.

Inflammatory lesions of acne may be divided into two groups. Less severe cases of acne are associated with pustules and papules, as well as with non-inflammatory lesions. Papules are inflamed, red, tender bumps with no head that range from 2 to 5 mm in diameter. Pustules are papules that are superficial and contain grossly purulent material, that is they have a head with a white or yellow center. Depending on the number of papules and pustules present, papulopustular acne cases may be graded in a range from moderate to severe acne. Individuals with severe cases of papulopustular acne may also have one or two acne nodules or cysts.

More severe cases of acne are associated with nodules and cysts as a predominant lesion. Such individuals present with three or more nodules and typically also have multiple other inflammatory lesions, such as pustules and papules, and non-inflammatory lesions, such as comedones. Cysts and nodules are blockages of the oil glands of the skin that have burst open and produced inflammation and pus in the surrounding tissues. Nodules are large, hard bumps 5 mm or more in diameter present under or within the surface of the skin, which can be painful and can last for many months. Cysts are similar to nodules but are pus-filled. Cases of acne presenting with inflammatory acne with cysts and/or nodules are often referred to as severe acne. However, since there is no accepted definition for the term "severe acne" and often papular or pustular acne is referred to as severe acne, it is preferred to refer to cases of acne presenting with cysts and/or nodules by the more specific term of "nodular" acne.

The Food and Drug Administration has recognized that nodular acne is a distinct entity that is to be considered independently of other, milder forms of acne. In the Draft Guidance for Industry—Acne Vulgaris: Developing Drugs for Treatment, issued in September 2005 by the U.S. Department of Health and Human Services, Food and Drug Administration, Center for Drug Evaluation and Research (CDER), the IGA Scale for Acne Vulgaris was utilized to grade the severity of non-nodular acne for the purposes of clinical trials of topical drugs. The IGA Scale for Acne Vulgaris, as depicted in the Draft Guidance for Industry, is as shown in Table 1.

TABLE 1

| Grade | Description |
|---|---|
| 0 | Clear skin with no inflammatory or noninflammatory lesions |
| 1 | Almost clear; rare noninflammatory lesions with no more than one small inflammatory lesion |
| 2 | Mild severity; greater than Grade 1; some noninflammatory lesions with no more than a few inflammatory lesions (papules/pustules only, no nodular lesions) |
| 3 | Moderate severity; greater than Grade 2; up to many noninflammatory lesions and may have some inflammatory lesions, but no more than one small nodular lesion |
| 4 | Severe; greater than Grade 3; up to many noninflammatory and inflammatory lesions, but no more than a few nodular lesions |

In the Draft Guidance for Industry, immediately below the IGA Scale, the FDA further distinguishes nodulocystic acne from other forms of acne and states that, "It is recommended that enrollment of acne vulgaris patients not include patients with nodulocystic acne." The Draft Guidance for Industry also states that because there are specific information needs with regard to treatment for nodular acne, applicants should seek additional guidance from the FDA regarding treatments that are targeted for nodular/nodulocystic acne.

Mild acne is typically treated with topical cleansers and benzoyl peroxide. Moderate inflammatory acne is often treated with cleansers and keratolytic or comedolytic agents such as retinoids (tretinoin, adapalene or tazaratene), salicylic acid or alphahydroxy acids, often in combination with topical or systemic antibiotics. Systemic antibiotics, including tetracycline, minocycline, doxycycline, erythromycin, and azithromycin, have been used successfully to treat pustular or papular acne. In May 2006, the Food and Drug Administration approved SOLODYN™ (minocycline HCl, Medicis Pharmaceutical Corp., Scottsdale, Ariz.) for treatment of non-nodular moderate to severe acne. The prescribing information on the package insert for Solodyn™ as approved by the FDA specifically states that "Solodyn™ is indicated to treat only inflammatory lesions of non-nodular moderate to severe acne vulgarism" To date, no antibiotic has been shown to be effective or has been approved by the FDA for treatment of nodular acne.

In cases of nodular acne, a dermatologist will often prescribe isotretinoin (ACCUTANE®, Roche Laboratories, Inc., Nutley, N.J.). Isotretinoin has been found to be effective in clearing nodular acne lesions. The drug works by reducing the size of oil glands in the skin so that much less oil is produced and the growth of bacteria is decreased.

The use of isotretinoin, however, has severe disadvantages. Isotretinoin has been shown to cause birth defects in the developing fetus and, therefore, pregnant women should not use isotretinoin. Additionally, isotretinoin has been associated with depression and suicidal thoughts in users. Because of the dangers associated with the use of isotretinoin, the FDA has initiated a program to permit only registered pharmacies and health care providers to dispense isotretinoin and to closely monitor the prescriptions and any adverse reactions occurring in patients receiving isotretinoin.

Because of the severe side effects of isotretinoin, there is currently no safe, approved therapy for treating nodular acne vulgaris.

Pigatto et al, "Isotretinoin versus Minocycline in Cystic Acne: A Study of Lipid Metabolism", Dermatologica, 172: 154-159 (1986) compared the efficacy of treatment of nodular cystic acne with isotretinoin and with minocycline, a member of the tetracycline family of antibiotics. Pigatto found that isotretinoin was highly efficacious in treating nodular cystic acne. In contrast, Pigatto found that, although minocycline was initially effective in reducing the number and size of nodules and cysts, treatment with minocycline beyond 4 weeks resulted in no further improvement. Moreover, treatment with minocycline did not, at any time during the study, decrease the number or size of cysts to a level that would be considered to be less than severe. As shown in FIG. 1 of Pigatto, treatment with minocycline reduced the number of cysts from an average of 20 to 10 during the first 10 weeks of treatment, but that further treatment with minocycline did not further decrease the number of cysts in the patients. Likewise, initial 10 week treatment with minocycline reduced the average diameter of cysts from 15 mm to 8 mm, but further treatment failed to produce any further reduction in diameter. In fact, after 20 weeks of treatment, average cyst diameter had increased once again to 10 mm. The Pigatto study establishes that minocycline is not an effective therapy for treatment of nodular acne.

The question of whether minocycline could be an effective therapeutic agent for nodular acne when used in combination with an additional anti-acne therapy was studied in Gollnick et al, "Comparison of Combined Azaleic Acid Cream Plus Oral Minocycline with Oral Isotretinoin in Severe Acne", Eur. J. Dermatol., 11:538-544 (2001). Golinick evaluated patients treated for six months with a combination of oral minocycline and topically applied azaleic acid cream and found that treatment after two months with this combination resulted in a decrease of 60% in number of deep acne lesions (cysts and nodules) and a decrease of 100% after four months. Thus, minocycline is an effective therapy for nodular acne when combined with topically applied azaleic acid.

The mode of action of minocycline and other tetracycline antibiotics in treating lesions of acne is uncertain. Ashley, U.S. Patent Application Publication No. 2004/0147492 discloses that tetracycline compounds, including minocycline and doxycycline, are effective in treating acne when administered to an individual in an amount that has substantially no antibiotic effect. The data of Ashley indicates that it is something other than the antibiotic effect of these drugs that provides the favorable anti-acne effect, although what the anti-acne mode of action of the tetracyclines is has not been determined. Because it is not the antibiotic activity of these compounds that provides their anti-acne effect, it is clear that one cannot extrapolate the level of effectiveness of tetracycline antibiotics in the treatment of acne to antibiotics that are not members of the tetracycline family.

Azithromycin is the generic name for 9-deoxo-9a-aza-9a-methyl-9a-homoerythromycin A, a broad spectrum antibiotic derived from erythromycin A. It was independently discovered by Bright, U.S. Pat. No. 4,474,768 and Kobrehel, U.S. Pat. No. 4,517,359, where it was referred to by the name of N-methyl-11-aza-10-deoxo-10-dihydroerythromycin A. Bright and Kobrehel disclosed azithromycin as a hygroscopic form. Allen, U.S. Pat. No. 6,268,489, discloses a non-hygroscopic dihydrate form of azithromycin. Both the monohydrate form and the dihydrate form are effective in treating bacterial infections when administered systemically.

Several scientific articles have published studies concerning the efficacy of azithromycin in treating lesions of inflammatory acne. Fernandez-Obregon, "Azithromycin for the Treatment of Acne," International Journal of Dermatology, 39:45-50 (2000), discloses that azithromycin administered in a pulse-dose regimen is as effective as other antibiotics tested in treating lesions of inflammatory acne.

Fernandez-Obregon compared daily systemic administration of doxycycline, erythromycin, minocycline, and tetracycline to three-times-weekly administration of azithromycin and found that the azithromycin treatment regimen was as effective as the daily treatment regimens of the other antibiotics in treating the lesions of inflammatory acne, even though azithromycin was administered at a much lower frequency than were the other antibiotics.

Treatment of acne with azithromycin, rather than with minocycline or doxycycline, is desirable because of the broad range of deleterious side effects that are experienced by users of minocycline and doxycycline. Minocycline use has been associated with skin discoloration, central nervous system effects such as dizziness and pseudomotor cerebri, and a lupus-like syndrome. Doxycycline use has been associated with gastrointestinal upsets, erosive esophagitis and photosensitivity. Both minocycline and doxycycline are also associated with candida vaginitis. Although there is some question as to whether azithromycin use may cause candida vaginitis, azithromycin has not been known to cause any of the other above side effects associated with minocycline or doxycycline. Additionally, minocycline and doxycycline are placed in Pregnancy Category D, which includes drugs that have some significant risks and that should be used during pregnancy only when the alternatives are worse. In contrast, azithromycin is a Pregnancy Category B drug, which category includes drugs that are used routinely and safely during pregnancy and which are considered safe to use if there is a clinical need for the drug.

The Fernandez-Obregon study treated patients suffering from at least 12 lesions of inflammatory acne, defined as papules, pustules, or cysts. Patients were graded on the reduction of the number of lesions associated with each treatment. The Fernandez-Obregon article did not distinguish between the various types of inflammatory lesions and it is possible, if not likely, that none of the patients treated had nodular or cystic lesions, or had at most one or two such lesions. Also, because nodular or cystic acne is considered to be a distinct form of acne requiring specific therapy and the intent of the Fernandez-Obregon study was to compare the efficacy of azithromycin to that of other antibiotics, which are known in the art to be efficacious to treat papular and pustular inflammatory lesions but not nodular or cystic lesions, it is evident to one of skill of the art that the patients treated in the Fernandez-Obregon study, although possibly having one or two cystic lesions, would not have been included in the study if they had been suffering from a distinct and more severe nodular acne.

A similar study was reported by Singhi, MK, et al, "Comparison of Oral Azithromycin Pulse with Daily Doxycycline in the Treatment of Acne Vulgaris," Indian Journal of Dermatology, Venereology, and Leprology, 69(4):274-276 (2003). Singhi compared azithromycin given at a dose of 500 mg for three consecutive days in a 10 day cycle with doxycycline given daily to a population of individuals suffering from moderate to severe inflammatory acne. Each of the individuals also received topical erythromycin therapy throughout the study.

Each of the patients was graded for severity of acne prior to commencement of therapy and at the end of therapy. The severity of acne was graded counting the number of comedones, papules, pustules, infiltrated, and cystic lesions, multiplying the number of each type of lesion by the lesions severity index (0.5 for comedones, 1 for papule, 2 for pustule, 3 for infiltrated lesion, and 4 for cyst), and summing the results.

Like Fernandez-Obregon, Singhi does not disclose that any of the subjects studied suffered from nodular acne and there is no suggestion that any of the subjects had multiple acne nodules. The results of Singhi were disclosed to be similar to those of Fernandez-Obregon and showed that azithromycin is an effective medication for treating moderate to severe acne vulgaris.

It is clear from the disclosures of Fernandez-Obregon and Singhi that nodular acne was not treated in their studies. Because an effective therapy for nodular acne that does not produce the severe side effects of isotretinoin has long been sought, if either of these studies had shown an effective antibiotic therapy against nodular or cystic acne, this result would have been proclaimed clearly as a breakthrough in acne therapy.

Accordingly, the need persists to the present day for an effective therapy for nodular acne that does not present severe side effects, such as those that occur with isotretinoin and possibly with tetracycline family antibiotic therapy.

DESCRIPTION OF THE INVENTION

The inventors have unexpectedly discovered that systemic administration of azithromycin is effective in treating nodules associated with acne, such as in patients suffering from nodular acne vulgaris. The inventors have further discovered that systemic administration of azithromycin is effective in treating the symptoms of severe nodular acne vulgaris.

As used herein, the term "acne" means acne vulgaris.

As used herein, the term "nodule" in the context of this application refers to an acne lesion that is a palpable solid lesion greater than 5 mm in diameter and which has depth within the skin.

As used herein, the term "acne (or inflammatory acne) with presence of nodules" refers to acne vulgaris in which one or more acne nodules are present in the skin.

As used herein, the term "nodular acne" or "nodular acne vulgaris" refers to acne vulgaris in which three or more acne nodules are present in the skin.

As used herein, the term "severe nodular acne" or "severe nodular acne vulgaris" refers to a case of acne vulgaris wherein an individual suffering from the acne vulgaris has five or more acne nodules present in the skin. Usually, patients with one or more acne nodules have additional manifestations of inflammatory acne, including multiple papular or pustular lesions.

The invention is a method for treating acne nodules, such as due to nodular acne vulgaris. According to the method of the invention, a patient suffering from acne nodules, such as from nodular acne vulgaris, is systemically administered azithromycin in a dosage and for a time sufficient to reduce the number of acne nodules present in the skin of the patient. This results in an improvement in the appearance and self-image of the patient and reduces or eliminates the significant pain and discomfort that are often associated with acne nodules. The patient may be afflicted with acne with presence of nodules or from a more severe form of acne, such as from nodular acne vulgaris or even from severe nodular acne vulgaris.

The azithromycin that is administered may be any pharmaceutically acceptable form of azithromycin that is effective in treating bacterial infections or acne. Preferred forms of azithromycin include the monohydrate and dihydrate forms, such as disclosed in U.S. Pat. Nos. 4,474,768; 4,517,359; and 6,268,489.

The patient of the method of the invention is typically a human but may also be a veterinary patient, such as a dog or cat. Human patients of the invention may be male or female and of any race and any age. Typically, the human patient of the invention is between 12 and 25 years old, although individuals younger than 12 years of age and older than 25 years of age are also suitable for the method of the invention.

Administration of azithromycin in accordance with the invention is by any route by which azithromycin may be systemically administered. Examples of routes of administration in accordance with the invention include parenteral routes, such as by intramuscular or subcutaneous injection, and oral routes, such as by swallowing tablets, capsules, liquids, or powders containing azithromycin.

Many different regimens for administration of azithromycin to treat acne vulgaris and bacterial diseases have been utilized. It is conceived that any of such regimens may be successfully utilized in connection with the method of the present invention. The amount of azithromycin that is administered in accordance with the invention is that which is effective to reduce the number of nodules in an individual afflicted with nodular or severe nodular acne vulgaris.

Thus, azithromycin may be administered in a pulsed dosing regimen. For example, azithromycin may be administered at a dosage of 250 mg of azithromycin for 3 or 4 days, followed by a period of non-administration of azithromycin for 3 to 7 days, and then repeated cycles of the 3 or 4 day administration and 3 to 7 day non-administration. If desired, a loading dose of azithromycin, such as 500 mg, may be administered prior to the commencement of the daily 250 mg azithromycin. An alternative pulsed dosing regimen is by repeated cycles of one week of daily administration of 250 mg of azithromycin followed by one week of no administration of azithromycin.

A preferred method of administration of azithromycin in accordance with the method of the invention is daily dosing, that is non-pulsed dosing, of azithromycin. In this method of administration, a dosage of azithromycin is administered daily until symptoms of nodular acne have lessened or have been eliminated.

Regardless of the dosing regimen that is utilized, administration of azithromycin may be continued for a duration sufficient to reduce or eliminate signs and symptoms of nodular acne vulgaris, such as a reduction in number of nodules. Preferably, there is a reduction of 66% or more in the number of nodules following treatment in accordance with the invention compared to the number present at the initiation of therapy. More preferably, the reduction is 75% or more. Most preferably, the reduction is 80% or more. In a most preferred embodiment, no nodules remain following treatment. Although an improvement in nodular acne may be obtained after only one or two weeks of treatment, a typical duration of therapy according to the invention is for a month or longer, and often for 2, 3, or more months.

If desired, the azithromycin may be administered in combination with other topical or systemic, such as oral, medications or therapies that are useful to treat the symptoms of acne. Skin cleansers and bactericidal agents such as benzoyl peroxide or azaleic acid and comedolytic and keratolytic agents such as salicylic acid, alphahydroxy acids, and retinoids such as tretinoin, adapalene and tazarotene, are often used in the treatment of acne. Topical antibiotics such as erythromycin, clindamycin, or tetracycline may be applied. It is preferred that no systemic antibiotic, other than azithromycin, be administered in accordance with the invention. Such combination systemic antibiotic therapy, even though not preferred, falls within the scope of the present invention. It is also within the scope of the invention to use azithromycin as described herein in conjunction with oral isotretinoin for the treatment of severe nodular acne. It is conceived that the administration of azithromycin may decrease the dose and duration of isotretinoin treatment needed, which is an important consideration considering the incidence and severity of side effects of isotretinoin, or may increase the overall clinical effectiveness of the isotretinoin regimen.

The invention is further illustrated by the following non-limiting examples. In the examples, patients included in the study were male or female subjects of any race, 16 years of age or older, presenting with 20-60 inflammatory lesions (papules or pustules), 20 to 150 non-inflammatory lesions (comedones or whiteheads), and 3 to 10 nodules.

EXAMPLE 1

Patients having severe acne vulgaris with multiple nodules were enrolled in an open label clinical study in which each patient received a daily oral dose of 250 mg of azithromycin for the 3-month duration of the study. Lesion counts were recorded at baseline before the initiation of treatment and at 1, 2, and 3 months following initiation of treatment. Of 18 patients that remained in the study longer than one month, only 2 did not respond favorably to treatment. These 2 patients had 9 and 8 nodules, respectively, at baseline and 8 and 13 nodules, respectively two months after initiation of therapy. Of the favorable responders, two patients who began the study with 3 nodules had 2 nodules at the end of the three month study. The remaining 14 patients who responded favorably to treatment had on average 6.7 nodules at baseline (range 4 to 10 nodules) and improved to having no nodules (10 patients) or at most 1 nodule (4 patients) by the end of the three month course of treatment.

EXAMPLE 2

Another set of patients with severe acne vulgaris was enrolled in an open label clinical study as in Example 1, except that each patient received a daily oral dose of 250 mg of azithromycin for one week followed by one week of no azithromycin, which cycle was repeated for the 3-month duration of the study. Of 18 patients that remained in the study longer than one month, only 2 did not respond favorably to treatment. These 2 patients had 6 and 10 nodules, respectively, at baseline and 5 and 8 nodules, respectively, two months after initiation of therapy. Three patients had partial clearing of nodules during the study. These patients had 9, 10, and 6 nodules, respectively, at baseline and 3, 4, and 2 nodules, respectively, at the end of the study. The remaining 13 patients who responded favorably to treatment had on average 6.2 nodules at baseline (range 3 to 10 nodules) and improved to having no nodules (10 patients) or at most 1 nodule (3 patients) at the end of the three month course of treatment.

EXAMPLE 3

Another set of patients with severe acne vulgaris was enrolled in an open label clinical study as in Example 1, except that each patient received a daily oral dose of 125 mg of azithromycin for the 3-month duration of the study. Of 20 patients that remained in the study longer than one month, only 2 did not respond favorably to treatment. These 2 patients had 8 and 3 nodules, respectively, at baseline and 10 and 4 nodules, respectively two months after initiation of therapy. The 18 patients who responded favorably to treatment had on average 5.1 nodules at baseline (range 3 to 8 nodules) and improved to having no nodules (13 patients) or at most 1 nodule (5 patients) at the end of the three month course of treatment.

Data from Examples 1 to 3 is summarized in Table 2.

TABLE 2

| | Example 1 250 mg/day | Example 2 250 mg/day every other week | Example 3 125 mg/day | Total Examples 1 to 3 |
|---|---|---|---|---|
| Number of patients | 18 | 18 | 20 | 56 |
| Number of good responders | 16 | 16 | 18 | 50 |
| Percentage of good responders | 88.9 | 88.9 | 90.0 | 89.3 |
| Number of nodules | 117 | 115 | 103 | 335 |
| Nodules remaining after treatment | 29 | 25 | 19 | 73 |
| Percentage of nodules cleared | 75.2 | 78.3 | 81.6 | 78.2 |
| Number of nodules in good responders | 100 | 99 | 92 | 291 |
| Nodules in good responders after treatment | 8 | 12 | 5 | 25 |
| Percentage of nodules cleared in good responders | 92.0 | 87.9 | 94.6 | 91.4 |

As shown in Examples 1 to 3 and in Table 2, systemic administration of azithromycin is highly efficacious in treating nodular acne vulgaris, including severe nodular acne vulgaris The above data shows that about 90% of individuals suffering from severe nodular acne who were treated with systemic azithromycin in accordance with the invention responded favorably to such treatment and that, in individuals responding favorably to this treatment, more than 90% of nodules were cleared.

The method of the invention provides a significant advance in the treatment of nodules associated with acne as it provides a therapeutic option for treating such difficult cases of acne that obviates the need to use isotretinoin, or reduces the amount or duration of isotretinoin therapy that would otherwise be used. Additionally, treatment of acne nodules with azithromycin is more effective than treatment with tetracycline antibiotics such as minocycline or doxycycline. The method of the invention, therefore, provides a valuable alternative in the treatment of acne nodules, which is especially advantageous in view of the presence of side effects that occur with minocycline and doxycycline therapy.

Further modifications, uses, and applications of the invention described herein will be apparent to those skilled in the art. It is intended that such modifications be encompassed in the following claims.

The invention claimed is:

1. A method for treating acne vulgaris nodules in an individual suffering therefrom comprising systemically administering azithromycin to the individual in an amount and for a time sufficient to decrease the number of acne nodules present in the skin of the individual.

2. The method of claim 1 wherein the individual is suffering from inflammatory acne with the presence of one or more acne nodules.

3. The method of claim 1 wherein the individual is suffering from nodular acne vulgaris.

4. The method of claim 1 wherein the individual is suffering from severe nodular acne vulgaris.

5. The method of claim 1 wherein azithromycin is the sole agent systemically administered to the individual for the treatment of acne vulgaris.

6. The method of claim 1 wherein the systemic administration of the azithromycin is oral.

7. The method of claim 1 wherein the azithromycin is administered to the individual in a dosage regimen lasting one month or longer.

8. The method of claim 1 wherein the azithromycin is administered daily.

9. The method of claim 1 wherein the azithromycin is administered in a pulsed-dosing regimen.

10. The method of claim 1 wherein the average dosage of azithromycin administered over the course of treatment is 250 mg/day or less.

11. The method of claim 10 wherein, during each day of the course of treatment, the azithromycin is administered at a dosage of 250 mg or less.

12. The method of claim 11 wherein, during each day of the course of treatment, the azithromycin is administered at a dosage of 125 mg or less.

13. The method of claim 1 wherein the azithromycin is administered in conjunction with a systemic medication effective for treating acne vulgaris.

14. The method of claim 13 wherein the systemic medication is isotretinoin.

15. The method of claim 1 wherein the azithromycin is administered in combination with one or more topical anti-acne therapies or medications.

16. The method of claim 15 wherein the topical anti-acne medication is a retinoid.

* * * * *